United States Patent [19]

Morén et al.

[11] 4,174,712
[45] Nov. 20, 1979

[54] DEVICE FOR USE WITH MEDICINAL INHALATION DEVICES

[75] Inventors: Nils F. E. Morén, Staffanstorp; Kjell I. L. Wetterlin, Sandby, both of Sweden

[73] Assignee: Aktiebolaget Draco, Lund, Sweden

[21] Appl. No.: 849,257

[22] Filed: Nov. 7, 1977

[30] Foreign Application Priority Data

Nov. 9, 1976 [SE] Sweden ............................. 7612448

[51] Int. Cl.² .................................... A61M 15/00
[52] U.S. Cl. ............................. 128/173 R; 128/201; 128/208; 128/209; 239/428.5; 137/171 R; 55/257 R; 48/180 A
[58] Field of Search ............... 128/201, 173 R, 173.2, 128/186, 187, 193, 194, 195, 196, 197, 203, 205, 209, 210, 192; 239/428.5; 137/171 R; 55/257 R, 319; 48/180 A

[56] References Cited

U.S. PATENT DOCUMENTS

| 673,021 | 4/1901 | Hidden | 128/201 |
|---|---|---|---|
| 1,854,726 | 4/1932 | Ziegler | 128/173 R |
| 2,906,463 | 9/1959 | Curry | 128/173 R X |
| 3,001,524 | 9/1961 | Malson et al. | 128/173 R |
| 3,522,806 | 8/1970 | Szekely | 128/173 R |
| 3,897,779 | 8/1975 | Hansen | 128/266 |

FOREIGN PATENT DOCUMENTS 325378 3/1935 Italy ...................................... 128/193

Primary Examiner—Henry J. Recla
Attorney, Agent, or Firm—Brumbaugh, Graves, Donohue & Raymond

[57] ABSTRACT

A device for use with a medicinal inhalation device comprises a rotationally symmetrical chamber having an opening to be connected to a spray nozzle and a mouthpiece. The chamber diverges conically from the opening and converges towards the mouthpiece. During passage through the chamber, an aerosol mist will lose propellant by evaporation, and smaller particles will be generated which can more readily follow the path of inhalation.

4 Claims, 1 Drawing Figure

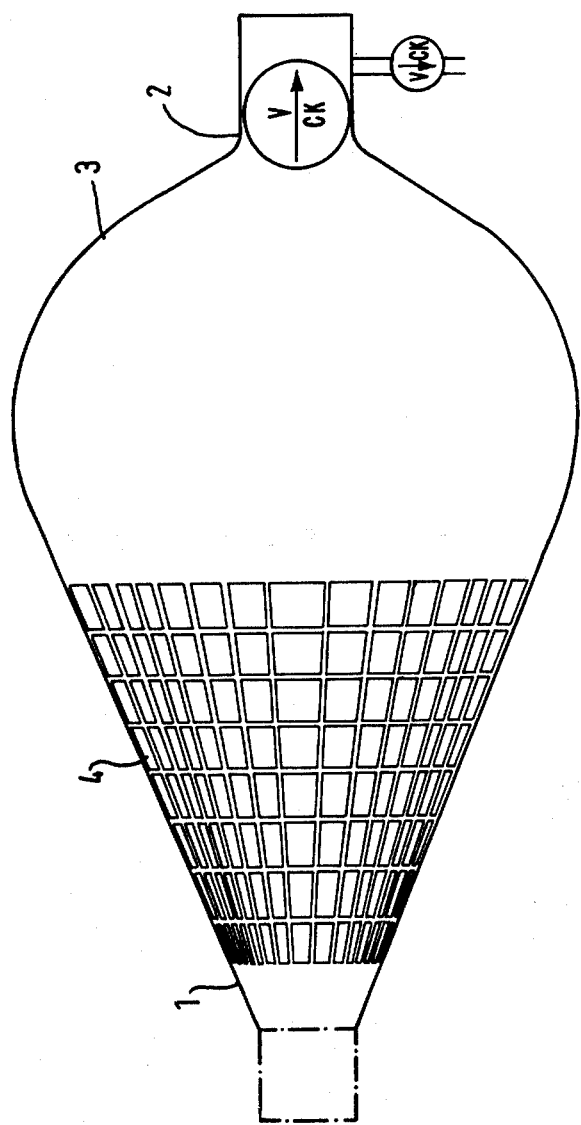

DEVICE FOR USE WITH MEDICINAL INHALATION DEVICES

The present invention relates to a devise for use with medicinal inhalation devices.

Aerosol inhalation devices for medicinal purposes are primarily used for local administration of drugs to the deeper parts of the respiratory tract. The advantage of local administration, as compared with systemic administration, is a rapid response to the drug even when a low dose of drug is administered.

Conventional aerosol inhalation devices, such as the devices disclosed in U.S. Pat. Nos. 3,001,524 and 3,897,799, can suffer from the following disadvantages;

1. A substantial part of the active compound is deposited on the walls of the mouthpiece or delivery tube, and is thereby lost.

2. A substantial part of the active compound is deposited in the oral cavity and is swallowed. The deposited portion of the dose may cause local side-effects, such as growth of fungi in certain parts of the oral cavity in the case of steroids, or systemic side-effects after absorption in the digestive system.

3. The activation of the aerosol inhalation device and the inhalation itself must be strictly co-ordinated when using conventional devices. Many patients do not manage this, and in such cases the effect of the drug is reduced.

4. With conventional aerosol inhalation devices, all the propellant is inhaled together with the active compound. This reduces the margin of safety, because the normal propellants are not considered to be completely non-toxic.

According to the present invention there is provided a device for use with a medicinal inhalation device and for generating and enclosing a delimited medicinal aerosol mist, the device comprising a rotationally symmetrical chamber, with an opening at one end to be connected with a spray nozzle and a mouthpiece at the other end, the axes of the mouthpiece and opening being aligned with the axis of symmetry of the chamber, the part of the chamber adjacent the opening being conical and diverging away from the opening, and the part of the chamber adjacent the mouthpiece converging towards the mouthpiece, the conical part of the chamber adjacent the opening being provided with orifices, the converging part of the chamber adjacent the mouthpiece not having orifices, the total internal volume of the chamber being between 0.5 and 2.0 liters, the total length of the chamber being between 10 and 40 cm, the maximum diameter of the chamber being between 25 and 80% of its length, and the part of the chamber which has the maximum diameter being closer to the mouthpiece than to the opening.

When used with an inhalation device, the device of the invention can reduce the above problems.

It has been realised that the deposition of the aerosol particles in the oral cavity and the upper respiratory tract is dependent on the size and velocity of the particles. Particles which are too big may not follow the change of direction of the inspiratory air, but impinge the walls and be deposited. This effect will be more clearly pronounced with increased particle size and velocity. The deposition may, therefore, be reduced by diminishing the particle size, which may be achieved by allowing the propellant to evaporate. With a pressurized container the aerosol particles are initially given a high kinetic energy, and, therefore, the speed of the particles should be reduced so that they mainly follow the direction of flow of the inspiratory air.

This is achieved with the device of the invention, which is designed to generate and enclose delimited medicinal aerosol mist, essentially free of propellant, intended for inhalation by one or more breaths via a mouthpiece.

The invention will be more clearly understood from the following description which is given by way of example only with reference to the accompanying drawing which shows a side view of a device of the invention.

The device of the invention which essentially comprises a chamber open at both ends and rotationally symmetrical, is based on the idea of using an attachment device to a conventional aerosol inhalation device, and to design this attachment device so that it corresponds with the conical shape of the aerosol mist generated from the spray nozzle. The part 1 of the chamber which is to be next to the spray nozzle is thus in the form of a cone, so that the deposition of active compound in the chamber will be exceedingly small.

Extending from the part 1, the chamber has a continually converging part 3 leading to a mouthpiece 2. The part 3 of the chamber may also be conical, and its function is to slow down the aerosol mist and generate an aerosol mist of smaller particles.

This last-mentioned effect is obtained due to the continuous evaporation of propellant from the aerosol droplets or particles during their passage from the spray nozzle. Their mass, kinetic energy and speed decrease (due to air resistance) and gradually, at 10 to 40 cm from the spray nozzle, they become sufficiently small to follow the change of direction of the inspiratory air.

The active compound in a medicinal aerosol is usually in the form of micronized dry substance with a particle size of less than 10 $\mu$m, suspended in a mixture of liquid fluorocarbon propellant such as Freon (Registered Trade Mark) in a pressurized container. Usually, the suspension consists of more than 99% by weight of liquid propellant. With the invention particle size and particle distribution in the aerosol mist to be inhaled will, due to the fact that the propellant is allowed to more completely evaporate, be reproducible and can be adapted so that the deposition in the oral cavity and the throat will be negligible compared to the amount deposited in the lungs.

The volume of the chamber should be great enough (0.5 to 2.0 liter) to correspond to one to four breaths. The length of the chamber should be between 10–40 cm, and preferably between 20–40 cm. By temporarily collecting the aerosol mist in the chamber, the aerosol particles can be inhaled by more than one subsequent inhalation, and the usual need for co-ordination between dispensing (via the spray nozzle) and inhalation is completely removed.

The conical part 1 of the chamber to be located next to the spray nozzle is equipped with orifices 4 which may occupy between 1 and 50%, and preferably between 10 and 50%, of the total surface area of the chamber and are preferably symmetrically arranged. An appreciable amount of the propellant which is evaporated from the aerosol droplets after their expulsion from the spray nozzle can thus diffuse out through these orifices and thus become separated from the aerosol droplets in the chamber. This separation takes place without any appreciable loss of aerosol droplets through the orifices, due to the fact that the aerosol droplets are relatively large and possess a high kinetic energy and speed compared to the surrounding air.

Because the orifices cover a comparatively large area, the particles may then easily be inhaled, in the form of a substantially propellant-free aerosol mist. The size and shape of the orifices is not critical, and can be varied within wide limits. For example, the orifices may alternatively consist of a fine-meshed net.

In order to avoid creating disturbing air currents when the inhalation of the aerosol mist takes place, it is essential that the converging part 3 of the chamber next to the mouthpiece 2 does not contain any orifices. For the same reason, the orifices on the conically shaped part, of the chamber to be next to the spray nozzle should preferably be placed rather close to the end of the chamber.

In order to obtain the best possible separation between propellant and active compound, the aerosol should be dispensed through the spray nozzle into the chamber a few seconds before the inhalation is started.

It is evident that a skilled worker can modify the device according to the invention in several ways without loosing the advantages connected with the invention. For example, the chamber may advantageously be divided into several sections, or be in the form of a folding bellows, in order to reduce its volume when not in use. When the chamber consists of a folding bellows, it may suitably be provided with a longitudinally acting helical spring in order to help maintain the chamber in its working configuration.

The chamber may be made in any suitable material, for example glass, plastics or metal. In a preferred embodiment, the mouthpiece is provided with a valve mechanism which makes it possible to exhale through the mouthpiece without the exhaled air passing through the chamber, and thus avoids the need to take the mouthpiece out of the mouth when exhaling. This valve mechanism may for example consist of two automatic non-return valves, one of them placed between the chamber and the mouthpiece, and the other placed on the side of the mouthpiece. While inhaling, the valve between the chamber and the mouthpiece is open, and the other valve closed. While exhaling, the first valve is closed and the other open. By using such an arrangement, the patient does not need to take the mouthpiece out of the mouth when exhaling, which simplifies the use of the device and even further reduces the need for co-ordination between dosage dispensing and inhalation.

Comparative tests with a conventional aerosol inhalation device, with and without a device according to the invention, have shown that the deposition of active compound in the oral cavity of the patient is diminished to less than a third when using a device according to the invention. Moreover, the deposition of active compound on the walls of the device was found to be negligible.

We claim:

1. A device for use with a medicinal inhalation device for generating and enclosing a delimited aerosol mist, the device comprising a chamber which is rotationally symmetrical about an axis and has opposed ends, an opening at one said end to be connected with a spray nozzle, and a mouthpiece at the other said end, said opening and mouthpiece having axes aligned with said axis, the chamber having a first part adjacent the opening and a second part adjacent the mouthpiece, said first part being conical and divergent away from the opening, said second part converging towards the mouthpiece, orifices being provided in said first part only, said orifices comprising 1–50% of the total surface area of the chamber, the total internal volume of the chamber being between 0.5 and 2.0 liters, the total length of the chamber being between 10 and 40 cm, the maximum diameter of the chamber being between 25 and 80% of its length, and the part of the chamber which has the maximum diameter being closer to the mouthpiece than to the opening.

2. A device as claimed in claim 1 wherein said second part of the chamber is conical.

3. A device as claimed in claim 1 wherein said orifices comprise between 10 and 50% of the total surface area of the chamber.

4. A device as claimed in claim 1 including, in said mouthpiece, a valve mechanism allowing exhalation through the mouthpiece without exhaled air passing through the chamber.

* * * * *